(12) United States Patent
Miller et al.

(10) Patent No.: US 9,121,073 B2
(45) Date of Patent: *Sep. 1, 2015

(54) PLUG-IN ELECTRIC VEHICLE SUPPLY EQUIPMENT WITH INDICATORS

(75) Inventors: Garret Miller, Owatonna, MN (US); Michael Muller, Harper Woods, MI (US); Charles K. Yankitis, New Baltimore, MI (US); Matthew C. Schuping, Concord Township, OH (US); David P. Futkos, Willoughby, OH (US)

(73) Assignee: Bosch Automotive Service Solutions Inc., Warren, MI (US)

( * ) Notice: Subject to any disclaimer, the term of this patent is extended or adjusted under 35 U.S.C. 154(b) by 368 days.

This patent is subject to a terminal disclaimer.

(21) Appl. No.: 13/485,213

(22) Filed: May 31, 2012
(Under 37 CFR 1.47)

(65) Prior Publication Data

US 2013/0063075 A1    Mar. 14, 2013

Related U.S. Application Data

(63) Continuation-in-part of application No. 12/646,276, filed on Dec. 23, 2009, now Pat. No. 8,710,796.

(60) Provisional application No. 61/229,104, filed on Jul. 28, 2009.

(51) Int. Cl.
*H02J 7/00* (2006.01)
*C12R 1/225* (2006.01)

(52) U.S. Cl.
CPC ............. *C12R 1/225* (2013.01); *A23V 2002/00* (2013.01)

(58) Field of Classification Search
CPC ... Y02T 90/14; Y02T 10/7005; Y02T 90/128; Y02T 10/7088; Y02T 90/163
USPC ........................................................ 320/109
See application file for complete search history.

(56) References Cited

U.S. PATENT DOCUMENTS

| | | |
|---|---|---|
| 4,820,187 A | 4/1989 | May |
| 5,462,439 A | 10/1995 | Keith |
| 5,548,200 A | 8/1996 | Nor et al. |
| 5,563,491 A | 10/1996 | Tseng |
| 5,721,481 A | 2/1998 | Narita et al. |

(Continued)

FOREIGN PATENT DOCUMENTS

WO    2010055411 A1    5/2010

OTHER PUBLICATIONS

International Search Report issued in PCT/US2013/043503 dated Dec. 23, 2013.

(Continued)

*Primary Examiner* — Arun Williams
(74) *Attorney, Agent, or Firm* — Baker & Hostetler LLP

(57) ABSTRACT

A system for connecting an electric vehicle to a high voltage power source. The system including electric vehicle supply equipment (EVSE) having an electrical plug compatible with a high voltage power outlet, the plug connected to a power cord. The power cord is connected to a housing containing a number of electrical components configured to control the power flow to an electric vehicle to recharge the vehicle's batteries. The housing includes a plurality of light emitting diodes configured to indicate a status of the EVSE. The LEDs can flash, illuminate a solid color, not illuminate a solid color or a combination thereof.

19 Claims, 5 Drawing Sheets

(56) References Cited

U.S. PATENT DOCUMENTS

| | | |
|---|---|---|
| 5,803,215 A | 9/1998 | Henze et al. |
| 6,198,251 B1 | 3/2001 | Landon |
| 6,316,908 B2 | 11/2001 | Kajiura |
| 6,483,272 B1 | 11/2002 | Terada et al. |
| 6,833,683 B2 | 12/2004 | Winkler |
| 6,905,362 B2 | 6/2005 | Williams |
| 6,951,206 B2 | 10/2005 | Kishimoto |
| 7,253,584 B2 | 8/2007 | Souther et al. |
| 7,254,468 B2 | 8/2007 | Pillar et al. |
| 7,278,878 B2 | 10/2007 | Draggie et al. |
| 7,579,807 B2 | 8/2009 | Funabashi et al. |
| 7,690,453 B2 | 4/2010 | Kinoshita et al. |
| 8,085,034 B2 | 12/2011 | Sirton |
| 8,111,043 B2 | 2/2012 | Redmann |
| 8,143,842 B2 | 3/2012 | Tyler et al. |
| 8,151,916 B2 | 4/2012 | Gearhart |
| 8,299,754 B2 | 10/2012 | Hayashigawa et al. |
| 2009/0140691 A1* | 6/2009 | Jung .............................. 320/108 |
| 2009/0313098 A1 | 12/2009 | Hafner et al. |
| 2010/0017249 A1 | 1/2010 | Fincham et al. |
| 2010/0174667 A1 | 7/2010 | Vitale et al. |
| 2010/0241560 A1 | 9/2010 | Landau-Holdsworth et al. |
| 2010/0268406 A1 | 10/2010 | Ito et al. |
| 2011/0029146 A1 | 2/2011 | Muller et al. |
| 2011/0074351 A1 | 3/2011 | Bianco et al. |
| 2011/0169447 A1 | 7/2011 | Brown et al. |

OTHER PUBLICATIONS

International Search Report & Written Opinion for PCT/US2012/040462, mailed Aug. 27, 2012.

International Search Report & Written Opinion for PCT/US2011/066380, prepared Jun. 13, 2012.

Robert Krause, et al., "Solid-State Relays Simplify Monitoring Electric-Car Battery Voltage," EDN, Feb. 19, 2004, 83-84.

* cited by examiner

PLUG-IN ELECTRIC VEHICLE SUPPLY EQUIPMENT WITH INDICATORS

CROSS-REFERENCE TO RELATED APPLICATIONS

This application is a continuation-in-part and claims priority to U.S. patent application Ser. No. 12/646,276, filed on Dec. 23, 2009, entitled "Plug-In Electric Vehicle Supply Equipment," which claims priority to U.S. Provisional Application No. 61/229,104, filed on Jul. 28, 2009, entitled "Plug-In Electric Vehicle Supply Equipment," both applications are incorporated herein by reference in their entirety.

FIELD OF THE INVENTION

The present invention relates generally to providing power to recharge the batteries of battery electric vehicles and plug-in hybrid electric vehicles. More particularly, the present invention relates to electric vehicle power supply equipment to deliver greater than 120 volts and 15 or 20 amps from an electrical socket.

BACKGROUND OF THE INVENTION

Vehicles powered either fully or partially by batteries must at some point recharge the batteries. Particularly in the case of battery electric vehicles, the lack of an alternative power source, like one that a plug-in hybrid electric vehicle would have, causes the batteries to deplete faster and have a more limited range. Plug-in electric hybrids are generally less taxing on the batteries and built-in regenerative systems may suffice to recharge the batteries enough to go longer without having to plug-in the vehicle to recharge it. However, the driver will dictate the need for recharging an electric vehicle through the extent of use, driving conditions, and driving style. High mileage, stop-and-go traffic, and quick accelerations are all things that the driver may subject an electric vehicle to, and all will deplete the batteries faster than under ideal conditions.

The standard American electrical socket provides 120 volts A/C. This electricity supply is often insufficient to recharge the batteries of an electric vehicle in a period of time to allow for convenient use of the electric vehicle. A full recharge may not even be completed overnight and partial recharges often take too much time to be practical. Providing a higher voltage electricity supply can greatly reduce the amount of time needed to recharge an electric vehicle. Such high voltage sources are available in homes and other locations.

It is desirable to provide a convenient way of connecting the high voltage electricity source to an electric vehicle to recharge the batteries thereby making recharging quicker and using an electric vehicle more practical. It is also desirable to provide a convenient way to plug the electric vehicle supply equipment to a 220/240V electrical supply source using plugs and receptacles designed to meet National Electrical Manufacturers Association (NEMA) standards. This will reduce the cost of the product, installation, service repair, relocation and greatly simplifying the local electrical permitting process. This will also make the electric vehicle more practical, acceptable and provide a lower cost of ownership for the vehicle consumer.

SUMMARY OF THE INVENTION

At least in view of the above, it would be desirable to provide a system for connecting a high voltage electricity source to an electric vehicle to recharge its batteries. The foregoing needs are met, to a great extent, by certain embodiments of the present invention. According to one such embodiment of the present invention, an apparatus for connecting an electric vehicle to an electrical socket includes a socket connector configured to couple with the electrical socket, a power conduit connected to the socket connector and configured to convey a voltage from the electrical socket, a power control device connected to the power conduit, a control circuit connected to the power conduit and configured to generate signals corresponding to the voltage along the power conduit, a vehicle connector configured to connect the power conduit to the electric vehicle, a processor connected to the control circuit and configured to receive signals from and send signal to the control circuit, and a housing to house at least the power conduit, the control circuit and the processor, wherein a plurality of light emitting diodes (LEDs) are on a surface of the housing to indicate a status of the apparatus.

In another embodiment, an apparatus for connecting an electric vehicle to an electrical socket includes means for coupling with the electrical socket, means for conveying a current from the electrical socket, the means for conveying the current being coupled to the means for coupling, means to control power connected to the means for conveying the current, a control circuit connected to the means for conveying the current and configured to generate signals corresponding to the current along the means for conveying the current, means for connecting the means for conveying the current to the electric vehicle, means for processing connected to the control circuit and configured to receive signals from and send signal to the control circuit, and means for housing at least the means for conveying the current, the control circuit and the means for processing, wherein a plurality of light emitting diodes (LEDs) are on a surface of the means for housing to indicate a status of the apparatus.

In yet another embodiment, a method of indicating a status of a vehicle charging apparatus includes the steps of receiving a high electrical voltage from a power source, conducting the high electrical voltage from the power source to the electrical vehicle via a power conduit, controlling the voltage flowing on the power conduit with a switching relay, isolating a processor from the voltage with a control circuit, and indicating a status of the vehicle charging apparatus with a plurality of light emitting diodes (LEDs).

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
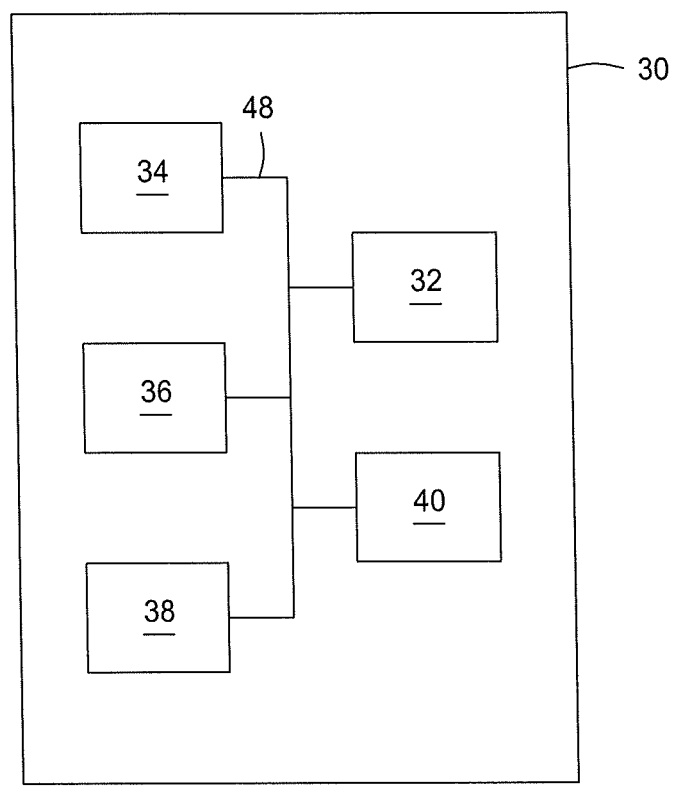
FIG. 1 is a block diagram view of an apparatus for connecting an electric vehicle to a high voltage power source according to an embodiment of the invention.

An embodiment of the present inventive system for connecting an electric vehicle, such as a battery electric vehicle (BEV) or a plug-in hybrid electric vehicle (PHEV), to a high voltage electricity source may include an apparatus for connecting the electric vehicle to a power source, or an electric vehicle supply equipment (EVSE). The EVSE may be employed to make a circuit connection to allow power from an electrical socket, like a wall socket, to flow to a charging circuit within the electric vehicle. The wall socket may be in a house or at a powering station outside the house. The power station may be positioned, for example, at a parking garage, at a public parking space, at a rest stop, a conventional gas station, or a power station. Further, the EVSE may be constructed to at least meet industry standards, such as SAE J1772, UL 2594, and NEC Article 625. The SAE J2836 vehicle communication standard may also be considered in constructing the EVSE.

The EVSE may have a socket connector at a first end to couple the EVSE to the electrical socket, such as a wall socket, and a vehicle connector at a second end to couple the EVSE to the electric vehicle. Once coupled, to both the wall socket and the vehicle, the EVSE may allow passage of electrical current from the wall socket to the electric vehicle, thus recharging the electric vehicles' batteries. This embodiment allows for the use of standard electrical outlets instead of hardwiring the EVSE to a power source.

In addition, the EVSE may analyze signals and/or data received from the electric vehicle. Analyzing the signals and/or data may involve checking the electric vehicle for specific conditions. While analyzing, the EVSE may determine when to allow and when to prohibit the flow of current between the socket and the electric vehicle.

The invention will now be described with reference to the drawing figures, in which like reference numerals refer to like parts throughout.

FIG. 1 is a block diagram view of an apparatus for connecting an electric vehicle to a high voltage power source according to an embodiment of the invention. An EVSE is one such apparatus and may include an input device 32, a memory 34, a communication device 36, a processor 38, and a display 40, some or all of which can be interconnected by a data link 48. The EVSE 30 can be a general computing device, such as a personal computer (PC), a UNIX workstation, a server, a mainframe computer, a personal digital assistant (PDA), a cellular phone, a smartphone, or some combination of these. Alternatively, the EVSE 30 can be a specialized computing device made up of components specifically chosen to execute the functionality of the EVSE 30. The remaining components can include programming code, such as source code, object code or executable code, stored on a computer-readable medium that can be loaded into the memory 34 and processed by the processor 38 in order to perform the desired functions of the EVSE 30.

The processor 38 may be executed in different ways for different embodiments of the EVSE 30. One embodiment is that the processor 38 is a device that can read and process data such as a program instruction stored in the memory 34 or received from a source on the electric vehicle. Such a processor 38 may be embodied by a microcontroller. On the other hand, the processor 38 may be a collection of electrical circuitry components built to interpret certain electrical signals and perform certain tasks in response to those signals, or an integrated circuit.

The memory 34 may include, for example, any form or combination of volatile, non-volatile, solid state, magnetic, optical, permanent, removable, writable, rewriteable, and read-only memory. The memory 34 may contain a number of program instructions for use with the EVSE 30. The instructions may include methods, for example, for controlling the flow of current between the electrical socket and the electric vehicle. These methods may include controlling when to allow or prohibit the flow of current, or perhaps moderate the flow of current. The flow of current can be controlled based on various factors such as when off peak rates of an electrical utility are in progress; the usage of power, for example, within a house, a building, a power grid, or a parking structure; the availability of current or if the current is constant; scheduled power outages; availability of raw materials that are used in generating electricity; the availability of alternative means of generating availability; the weather at the local charging station or outlet, which can effect means of generating electricity, such as wind mills, and solar panels and the like.

Further, the memory may contain software having instructions related to diagnosing vehicle functions, such as OBD-II, battery testing, tire pressure sensor testing, emissions testing and the like. Further, the software may include the ability to track the status of various batteries in the vehicles, such as which batteries have been replaced, the remaining battery life of the various batteries, the warranty information about the batteries, the type of batteries used in the vehicle (mix and match) and the like. Many other embodiments may provide for further methods, some of which will be discussed herein.

Additionally, an embodiment of the EVSE 30 can communicate information to a user through the display 40 and request user input through the input device 32 by way of an interactive, menu-driven, visual display-based user interface, or graphical user interface (GUI). The user may interactively input information using direct manipulation of the GUI. Direct manipulation can include the use of a pointing device, such as a mouse or a stylus, to select from a variety of selectable fields, including selectable menus, drop-down menus, tabs, buttons, bullets, checkboxes, text boxes, and the like. Nevertheless, various embodiments of the invention may incorporate any number of additional functional user interface schemes in place of this interface scheme, with or without the use of a mouse or buttons or keys, including for example, a trackball, a scroll wheel, a touch screen or a voice-activated system.

Some options that may be selected through the input device 32 may allow the user some control over the charging of the electric vehicle. The user may select, for example, that the batteries be charged to or at a certain level or for a certain amount of time, a certain number of charges or start and stop at a certain time or at a particular event. Further, the user may select to be notified on a separate device, like on a cellular device, smart phone, pager, fax, remote control/display, or other wired and wireless devices, that the electric vehicle or charging is in a certain state, such as complete or faulted. The user may be able to set the EVSE to control and power some of the vehicle components while plugged in. For example, during different seasons the user may desire to heat or cool the vehicle as he gets ready for work in the morning so that the vehicle is comfortable when he gets in it. The EVSE may also control setting the radio, power seats and mirrors depending on user preferences. Through the use of the EVSE, other devices like a GPS, radar detector, and other devices that require boot or warm up periods may be powered on before the user enters the electric vehicle.

The display 40 may have a more simple implementation than previously mentioned, consisting of one or multiple indicators. Such indicators may consist of a small liquid crystal display (LCD) that can depict text or graphics. The LCD may be monochrome or colored. Other embodiments may include a single or multiple light emitting diodes (LED). This implementation could work for transmitting a limited number of simple messages. An LED may emit a single color of light, or it may be able to emit a number of different colors. Each LED or color may be associated with a different message. Some messages may include that power is available to charge the electric vehicle batteries, that charging the electric vehicle batteries is in progress, that the charging is complete, and that there is a fault or problem. The display may also be used to indicate the level of charge for the batteries, the number of times the batteries have been charged and the remaining charging time or the time the batteries have been charging.

Figure 2A:
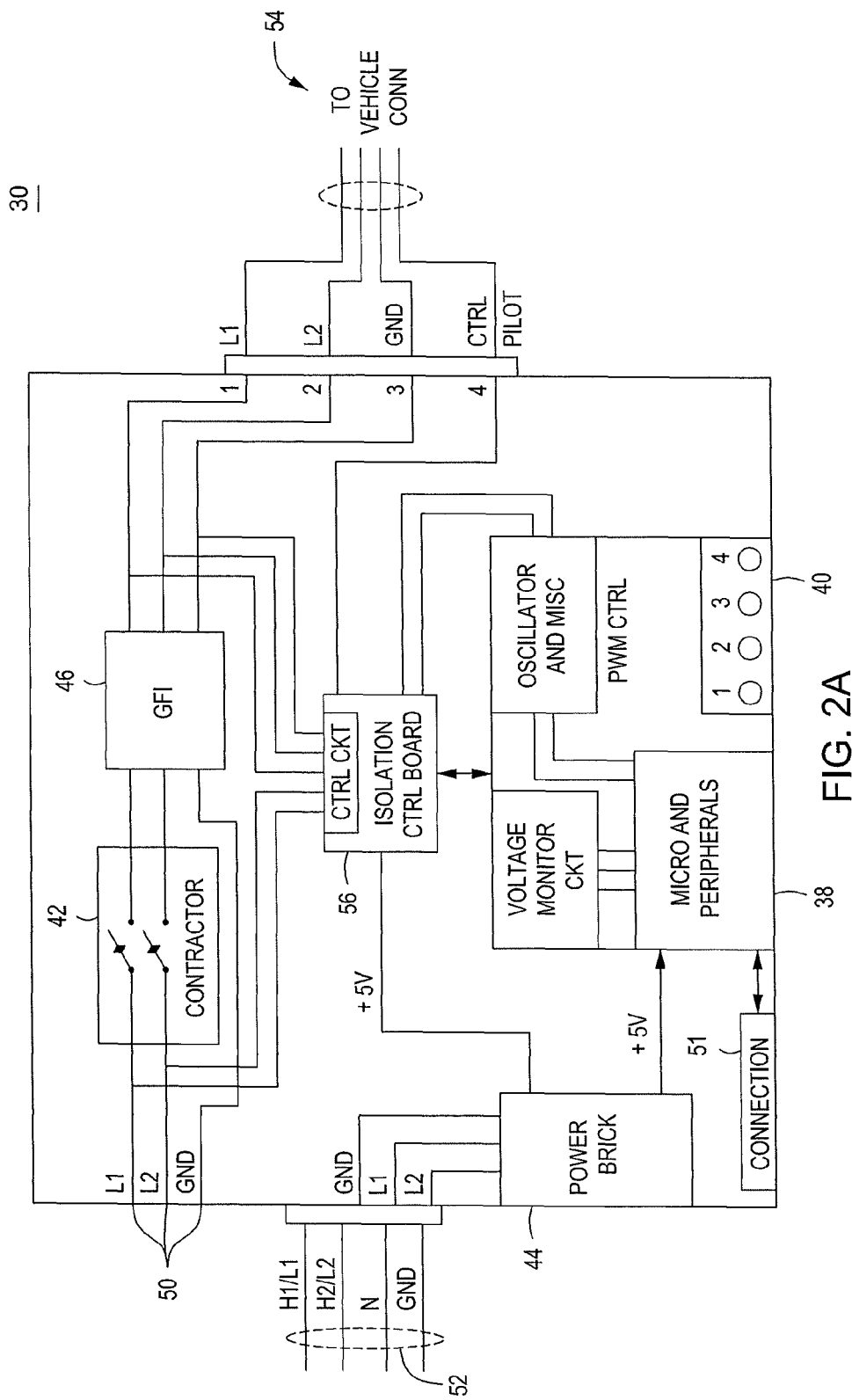
FIG. 2A is a schematic view of an apparatus for connecting an electric vehicle to a high voltage power source according to another embodiment of the invention.
Figure 2B:
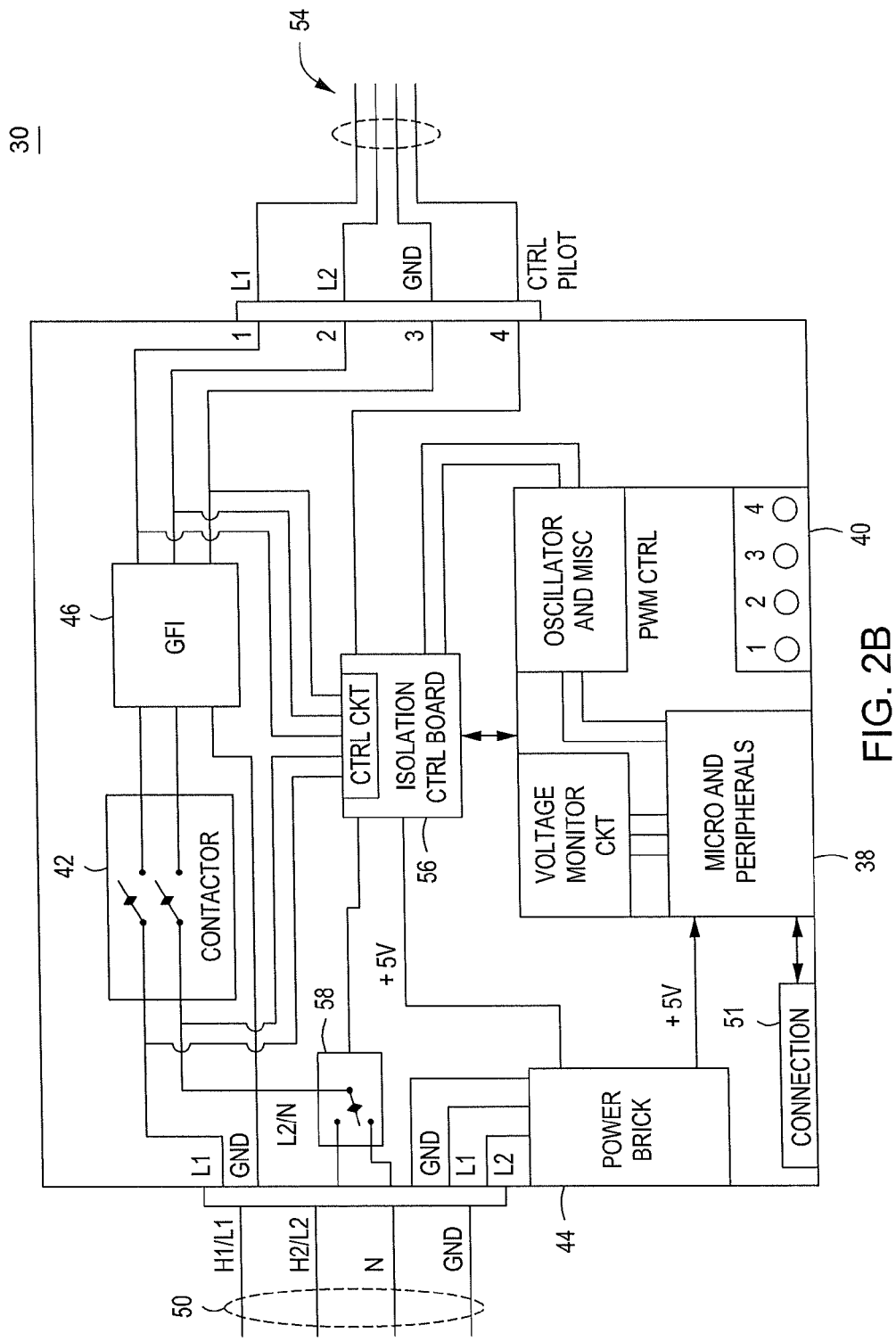
FIG. 2B is a schematic view of an apparatus for connecting an electric vehicle to a high voltage power source according to another embodiment of the invention.

Referring now to FIGS. 2A and 2B, the EVSE 30 may further include a relay 42, a voltage regulating device 44, and a breaking device 46, some or all of which may be connected by an electric conduit 50. A control circuit 56 may act as a buffer between different parts of the EVSE 30. At one of the EVSE is a socket connector 52 (explained below) and at the other end is the vehicle connector 54 (explained below).

The voltage regulating device 44 may be needed to power the electronic components of the EVSE 30. Since the EVSE 30 may draw its power from the same electrical socket it uses to charge the batteries of the electric vehicle, the EVSE 30 will be receiving high voltage electricity. The electrical socket may supply, for example 220 volts or 240 volts. The high voltage of the power drawn from the electrical socket could damage some of the electronic components of the EVSE 30. Thus, the voltage regulator device 44, such as a transformer or a voltage regulator, may be employed between to the electrical socket and the electrical components of the EVSE 30. The voltage may then be lowered to a level that is manageable to the electrical components, such as, for example, 5 volts or 12 volts. In other embodiments, the voltage regulator can increase the voltage as needed by the EVSE 30.

While the voltage regulating device 44 may regulate the voltage to parts of the EVSE 30, there are parts where electricity may flow unaltered from the electrical socket to the electric vehicle. An electric conduit 50 may run the length of the EVSE 30. However, it should not run uninterrupted. A relay 42 may be placed to bridge segments of the electric conduit 50, allowing the EVSE 30 to start and stop the flow of power to the electric vehicle. The electric conduit 50 may optionally be connected to a voltage regulator to step up or step down the voltage passed to the electric vehicle.

Also connected to the electric conduit 50 may be a breaking device 46 (also called a ground device or a current monitor). The breaking device 46 is intended to cut power along the electric conduit 50 quickly so as to avoid harming a user with a high voltage electric shock or harming the components of the EVSE. Such a breaking device 46 may be a ground fault interrupter. If the breaking device 46 trips and cuts power, EVSE 30 may have an auto-reset function to attempt to restore the power transfer to the electric vehicle. The auto-reset function may attempt to restore the power transfer after a determined time or for a determined number of tries. The auto-reset functions allow for continuous charging of the vehicle should a power surge occurs while the user is asleep or away from the charging location.

The control circuit 56 may be connected to the electric conduit 50 and to the data link 48. Acting as a buffer between two portions of the EVSE 30, the control circuit may pass signals from the electric conduit 50 representing the voltage on the electric conduit 50 to the processor 38. From these signals, the processor 38 may react accordingly to control the relay 42 and the breaking device 46. Further, the processor 38, and other components, such as a voltage monitor, an oscillator, and a pulse width modulator may act accordingly to conduct a number of functions of the EVSE 30. The control circuit 56 may also be connected to the voltage control device 44 for power, and a control pilot pin of a vehicle connector (discussed below) to pass on signals from the vehicle to the other components of the EVSE 30.

The EVSE also includes peripheral connection 51 that can add additional functionality to it, including USB, Fire-Wire, card reader, vehicle connector interface (for OBD-II, and the like connections), CD, DVD, memory, wireless communication, and additional hardware and software. The EVSE's software can be updated via the peripheral connection 51. Additional hardware can be added to include, for example, additional processor, memory, FPGA (field programmable gate array), ASIC, pin connections, multiplexor and the other hardware to expand the functionality of the EVSE.

Figure 3:
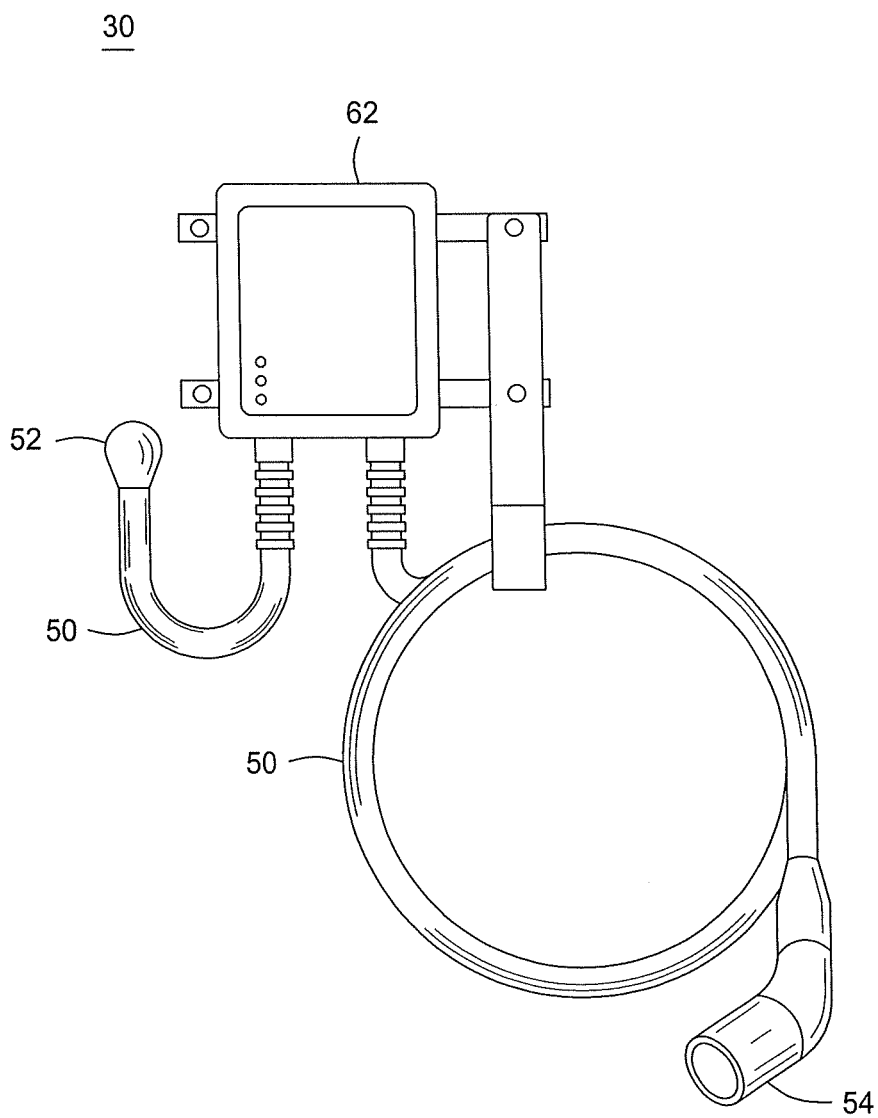
FIG. 3 is an elevation view of an apparatus for connecting an electric vehicle to a high voltage power source according to another embodiment of the invention.

Referring now, to FIG. 3, attached to a respective end of the electric conduit 50 may be the socket connector 52 and the vehicle connector 54. The socket connector 52 may couple with the electrical socket to allow electricity to flow to the EVSE 30. Any of a number of available or proprietary connectors may be used for the socket connector 52. Such available connectors may include a NEMA 14 plug, for example, a NEMA 14-50P plug if appropriate for the electrical socket. Connected to the opposite end of the electric conduit 50 may be the vehicle connector 54, which also may be any number of available or proprietary connectors. One such example of a vehicle connector 54 may be a five-pin connector including two power pins, a ground pin, a control pilot pin, and a proximity sensor pin as specified in the SAE standard J1772 and designed by Yazaki of North America.

In various embodiments, the EVSE 30 can be coupled to a communication network. The communication network allows for communication between the EVSE 30 and a remote device. The EVSE 30 can be coupled to the communication network by way of the communication device 36 which in various embodiments can incorporate any combination of devices—as well as any associated software or firmware—configured to couple processor-based systems. Such communication devices 36 may include modems, network interface cards, serial buses, parallel buses, LAN or WAN interfaces, wired, wireless or optical interfaces, and the like, along with any associated transmission protocols, as may be desired or required by the design.

The communication network links the communication device 36 of the EVSE 30 with the remote device. Various embodiments of the communication network may include any viable combination of devices and systems capable of linking computer-based systems, such as USB; Bluetooth; Wi-Fi; ZigBee; power line communication (PLC); home area network (HAN); Silver Spring network; stable election protocol (SEP); the Internet; TCP/IP; an intranet or extranet; a local area network (LAN); a wide area network (WAN); a direct cable connection; a private network; a public network; an Ethernet-based system; a token ring; a value-added network; a telephony-based system, including, for example, T1 or E1 devices; a cellular telephony system, for example, GPRS or GSM; an Asynchronous Transfer Mode (ATM) network; a wired system; a wireless system; an optical system; a combination of any number of distributed processing networks or systems or the like.

The remote device may be a common remote device, such as an electronic control unit of a vehicle, an example of which often used in vehicles for receiving diagnostic signals such an OBDII signals. The remote device may also be a proprietary remote device, such as one developed for use with a specific brand of engine or specific model of engine. Further embodiments may encompass the remote device being a data receiver for a tire pressure management system. In either of these cases, the communication device 36 may be able to connect with a dealer, manufacturer, service department, government entity such as a state inspection office, etc. and report the findings transmitted from the remote device.

Moreover, the remote device may be a wireless device with a display that gives the user information about the status of the electric vehicle connected to the EVSE 30. The remote device may be such that it is easily placed within a room in a building, or even attached to a key like a key chain. The information delivered to the user may include charge status of the vehicle, diagnostic messages, tire pressure management system messages, and other vehicle related information.

The EVSE 30 may also act as a remote control allowing the user to control function of the car, like power, air conditioning and heat, radio settings, power seat and mirror settings, etc. The EVSE 30 may also have internet access or similar communication access to remote server in order to obtain information such as emails, weather report, web pages, stock information, diagnostic databases and the other information.

The communication device 36 may also be able to communicate with the local utility company. This may allow for the utility company to know that the vehicle in connected and to charge the vehicle at a certain time of the day, such as during off-peak hours, if requested by the user. One embodiment to implement this feature is through the remote device, where the remote device encompasses a smart meter or a computerized utility meter. The EVSE 30 may communicate with the smart meter to determine when the EVSE 30 should charge the vehicle depending on certain parameters. If it is a goal to reduce energy costs, the smart meter may determine at what time of the day the rate for electricity is lowest, and during that time, tell the EVSE 30 to charge the vehicle. The EVSE 30 may also communicate with the smart meter to indicate when the vehicle is charging and how much charging is required. With this information the smart meter may be able to manage the power consumption of the rest of a house to keep overall power consumption at or below a desired level.

The EVSE 30 may include a housing 62. The housing 62 may encase a number of the components of the EVSE 30, for example, all the components previously mentioned except for portions of the electric conduit 50, the socket connector 52 and the vehicle connector 54. A bracket may be attached to the housing 62 to mount the housing 62 on a vertical surface such as a wall or post. The housing 62 or bracket may further include a hook to hang the power conduit 50. Alternatively, the power conduit may be retractable into the housing 62.

The EVSE 30 may be available for both indoor and outdoor applications. Proper weather proofing may be part of the housing to protect the components from damage and the users from injury. Some outdoor installations of the EVSE 30 may include burial in the ground, being attached to a post, or integrated into a pedestal.

Other embodiments of the EVSE 30 may allow for multiple power conduits 50, each with its own vehicle connector 54. The EVSE 30 may charge the vehicles simultaneously or switch from one vehicle to another after the first vehicle has completed recharging. There may also be an adapter that allows the socket connector to connect to low voltage sockets, such as ones that provide 120 volts or less. In other embodiments, the EVSE 30 can connect to alternative power sources that use renewable energy to charge the vehicle. Such sources may include solar panels and wind turbines, for example. If the alternative power sources alone are insufficient, then they may be supplemented by an electrical socket connected to a utility company source.

As stated above, the EVSE may potentially perform a variety of other functions in addition to its primary purpose of charging the electric vehicle. Multiple embodiments may also include any number of functions that may be considered secondary purposes of the EVSE. A few examples of these functions may include conducting battery tests and reporting the state of the batteries and the number of times the batteries have been charged. The EVSE may also conduct vehicle diagnostics, execute a tire pressure management system, run an emissions analysis, etc.

Figures 4, 5:
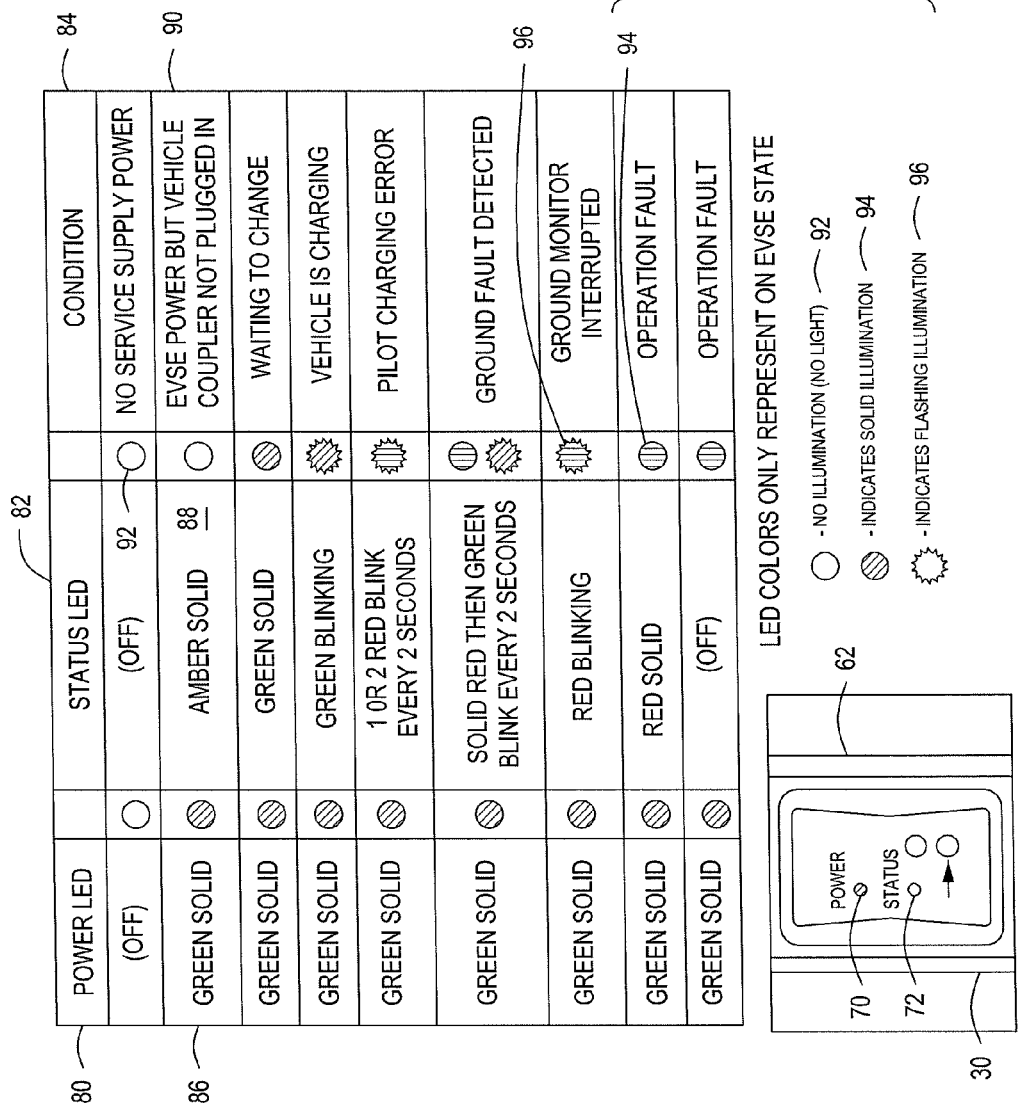
FIG. 4 is a front view of an apparatus having LEDs for connecting an electric vehicle to a high voltage power source according to an embodiment of the invention.
FIG. 5 is a chart of interpreting the LEDs of FIG. 4 according to an embodiment of the invention.

FIG. 4 is a front view of an apparatus having LEDs for connecting an electric vehicle to a high voltage power source according to an embodiment of the invention. The EVSE 30 includes the housing 62 having power LED 70, and status LED 72. Although only two LEDs are shown, the EVSE can have as many LEDs as desired by the user. Power LED 70 can be used to indicate whether the EVSE has power or is turned on and status LED 72 provides certain status information. In one embodiment, the power LED 70 indicates whether there is power being supplied to the EVSE or that the EVSE is turned on and status LED 72 indicates other status. In another embodiment, the LEDs 70, 72 can be used in combination to indicate status of the EVSE as shown in FIG. 5.

FIG. 5 is a chart for interpreting the LEDs of FIG. 4 according to an embodiment of the invention. In one embodiment, the LEDs 70, 72 may indicate in various ways including: (1) no illumination 92, (2) solid illumination 94, and (3) flashing illumination 96. In another embodiment, the LED may cycle through one or more of no illumination 92, solid illumination 94, and/or flashing illumination 96 so that as many combinations are possible to indicate as much information as desired.

The power LED indicator colors can be found under a power LED description column 80 while a status LED indicator colors can be found under the status LED column 82. Additionally, a condition column 84 describes the state of the EVSE based on the indicator's color of the power LED description column 80 (of power LED 70) and status LED column 82 (of status LED 72). In another embodiment, the condition column 84 can provide the description of the indicator color of the power LED description column 80 or status LED column 82.

By knowing the status of the EVSE 30 based on the LEDs 70, 72, the user can take corrective actions, such as determining why the EVSE is not receiving power or why the vehicle coupler is not plugged in. This way, the user is not surprised if the vehicle was not properly charged as he expected it to be when he gets into the vehicle. For example, if the power LED 70 is green solid 86 and the status LED 72 is amber solid 88, then the condition 90 is "EVSE power but vehicle coupler not plugged in." This allows the user to take corrective action, such as plugging the vehicle coupler to the vehicle.

Although FIG. 5 describes certain colors, description and statuses, this is not meant to be limiting and that other embodiments contemplate other colors (blue, orange, pink, black, etc.), descriptions and statuses. Additionally, the LED may include two or more colors or the intensity of the color of the LED may also indicate other status.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. An apparatus for connecting an electric vehicle to an electrical socket, comprising:
   a socket connector configured to couple with the electrical socket;
   a power conduit connected to the socket connector and configured to convey a voltage from the electrical socket;
   a power control device connected to the power conduit, wherein the power control device is a voltage regulator configured to step up or step down the voltage;
   a control circuit connected to the power conduit and configured to generate signals corresponding to the voltage along the power conduit;
   a vehicle connector configured to connect the power conduit to the electric vehicle;
   a processor connected to the control circuit and configured to receive signals from and send signal to the control circuit; and
   a housing to house at least the power conduit, the control circuit and the processor, wherein a plurality of light emitting diodes (LEDs) is on a surface of the housing to indicate a status of the apparatus, wherein the status includes that the apparatus has power but the vehicle connector is not connected to the electric vehicle.

2. The apparatus of claim 1, wherein the power control device includes an electrical relay configured to bridge portions of the power conduit.

3. The apparatus of claim 1, further comprising:
   a voltage monitor connected to the processor;
   a current monitor connected to the power conduit;
   a pulse width modulator connected to the processor; and
   a display connected to the processor.

4. The apparatus of claim 3, wherein a current monitor is a ground fault interrupter.

5. The apparatus of claim 1, wherein each of the plurality of the LEDs indicates the status of the apparatus through no illumination, solid illumination or flashing.

6. The apparatus of claim 1, wherein each of the plurality of LEDs goes through at least two of the following phases: a no illumination phase, a solid illumination phase and a flashing phase.

7. The apparatus of claim 1, wherein each of plurality of LEDs indicates the status of the apparatus by alternating between solid illumination and flashing.

8. The apparatus of claim 1, wherein the control circuit is connected to the vehicle connector.

9. The apparatus of claim 1, wherein the control circuit is configured to isolate the processor from the voltage along the power conduit.

10. The apparatus of claim 1, wherein the status is a fault in the apparatus.

11. An apparatus for connecting an electric vehicle to an electrical socket, comprising:
    means for coupling with the electrical socket;
    means for conveying a current from the electrical socket, the means for conveying the current being coupled to the means for coupling;
    means for controlling power connected to the means for conveying the current, wherein the means for controlling is configured to step up or step down a voltage;
    a control circuit connected to the means for conveying the current and configured to generate signals corresponding to the current along the means for conveying the current;
    means for connecting the means for conveying the current to the electric vehicle;
    means for processing connected to the control circuit and configured to receive signals from and send signal to the control circuit; and
    means for housing at least the means for conveying the current, the control circuit and the means for processing, wherein a plurality of light emitting diodes (LEDs) is on a surface of the means for housing to indicate a status of the apparatus, wherein the status includes that the apparatus has power but the means for connecting is not connected to the vehicle.

12. The apparatus of claim 11, wherein each of the plurality of the LEDs indicates the status of the apparatus through no illumination, solid illumination or flashing.

13. The apparatus of claim 11, wherein each of the plurality of LEDs goes through at least two of the following phases: a no illumination phase, a solid illumination phase and a flashing phase.

14. The apparatus of claim 11, wherein each of plurality of LEDs indicates the status of the apparatus by alternating between solid illumination and flashing.

15. The apparatus of claim 11, wherein the status is a fault in the apparatus.

16. A method of indicating a status of a vehicle charging apparatus, comprising the steps of:
    receiving a high electrical voltage from a power source;
    conducting the high electrical voltage from the power source to an electrical vehicle via a power conduit;
    controlling the high electrical voltage flowing on the power conduit with a switching relay;
    changing an amount of voltage by stepping up the voltage or stepping down the voltage with a voltage regulator;
    isolating a processor from the high electrical voltage with a control circuit; and
    indicating a status of the vehicle charging apparatus with a plurality of light emitting diodes (LEDs), wherein the status includes that the apparatus has power but a vehicle connector is not connected to the vehicle.

17. The method of claim 16, wherein the indicating step further comprising:
   not illuminating the plurality of LEDs.

18. The method of claim 16, wherein the indicating step further comprising:
   illuminating the plurality of LEDs.

19. The method of claim 16, wherein the indicating step further comprising:
   flashing the plurality of LEDs.

* * * * *